(12) United States Patent
Johnson

(10) Patent No.: US 11,602,664 B2
(45) Date of Patent: Mar. 14, 2023

(54) COMPACT LIGHTWEIGHT PERSONAL TRAINER

(71) Applicant: Sharon C. Johnson, Laurelton, NY (US)

(72) Inventor: Sharon C. Johnson, Laurelton, NY (US)

(*) Notice: Subject to any disclaimer, the term of this patent is extended or adjusted under 35 U.S.C. 154(b) by 321 days.

(21) Appl. No.: 16/886,384

(22) Filed: May 28, 2020

(65) Prior Publication Data

US 2021/0322819 A1    Oct. 21, 2021

Related U.S. Application Data

(60) Provisional application No. 63/013,439, filed on Apr. 21, 2020.

(51) Int. Cl.
| | |
|---|---|
| *A63B 21/00* | (2006.01) |
| *A61B 5/11* | (2006.01) |
| *G01C 22/00* | (2006.01) |
| *G16H 20/60* | (2018.01) |
| *G01G 19/50* | (2006.01) |
| *H04W 4/80* | (2018.01) |

(52) U.S. Cl.
CPC ........ *A63B 21/4037* (2015.10); *A61B 5/1118* (2013.01); *G01C 22/006* (2013.01); *G01G 19/50* (2013.01); *G16H 20/60* (2018.01); *H04W 4/80* (2018.02)

(58) Field of Classification Search
CPC ...... A63B 21/4037; H04W 4/80; G16H 20/60
See application file for complete search history.

(56) References Cited

U.S. PATENT DOCUMENTS

2012/0259378 A1* 10/2012 Heinrichs .............. G01G 19/52
                                                                       607/6
2016/0116327 A1*  4/2016 McCaskill ............. G01G 19/58
                                                                       177/1

FOREIGN PATENT DOCUMENTS

CN            111289074 A  *  6/2020  ............. G01G 19/44

* cited by examiner

*Primary Examiner* — Congvan Tran
(74) *Attorney, Agent, or Firm* — Handal & Morofsky LLC; Anthony H. Handal

(57) ABSTRACT

The inventive apparatus comprises a mat member. The mat includes a scale physically secured to the mat member. The scale has an electrical output strives an electronic circuit. A display displays a weight measured by the scale. A switch is distributed over an area roughly commensurate with the area needed to trot in place. The switch is secured to the mat and underlies a top surface of the mat. The switch is coupled to the electronic circuit. The electronic circuit is programmed to count the number of times that the switch is closed, whereby trotting in place results in closing the switch in response to trotting paces. The above transducers are used to monitor and crosscheck activity and dietary information input into the system by the user and make recommendations.

15 Claims, 4 Drawing Sheets

COMPACT LIGHTWEIGHT PERSONAL TRAINER

TECHNICAL FIELD

The invention relates to a compact lightweight portable personal physical fitness training device meant to take the place of a human personal trainer by providing functionalities for maintaining and/or monitoring physical fitness and spiritual wellness and for facilitating, enabling and planning yoga, exercise, and related health and spiritual regimens in response to transducers for collecting data.

CROSS REFERENCE TO RELATED APPLICATIONS (Not applicable)

STATEMENT REGARDING FEDERALLY SPONSORED RESEARCH OR DEVELOPMENT (Not applicable)

BACKGROUND OF THE INVENTION

The invention relates to a mat-like device for facilitating exercise and physical and mental well-being, while at the same time monitoring, recording and planning activities. The inventive method may be used as a yoga mat for practicing yoga as well as other physical activities.

Yoga mats have been known for many years. More particularly, yoga was typically practiced on kusha grass, directly on compressed dirt floors, or on a rug, for example one made of animal skin.

Today, typical floor coverings may not lend themselves to the practice of yoga or other exercises. For example, wooden floors in gymnasiums are covered with rubber mats which facilitate gripping balance and other needs and are, for many purposes, advantageous as compared to wooden floors. Likewise, homes often have wooden floors and/or rug floor coverings neither of which present ideal surfaces for many physical activities, including yoga. Yoga mats are specially fabricated mats which are made to address those needs. For example, a yoga mat will help prevent the hands and feet from slipping during asana practice in modern yoga, as well as during exercise. This function is alluded to in the term "sticky mat" which was used to describe yoga mats when they first started to become popular about fifty years ago. These mats, sometimes made of rubber, replaced the use of towels or cotton mats on wooden floors. These rubber mats reduce the tendency of feet to slip and skid on the cotton. Likewise, the good grip provided by a rubber mat reduced the amount of strength needed to maintain certain yoga positions.

Modern yoga mats are suitable for energetic exercise, as well as various forms of yoga. They are made of plastic, rubber, and sometimes other materials including hessian and cork. Proper design involves a balancing of comfort during use and effectively providing a good gripping surface. At the same time, economical construction is also important. Finally, another factor is the overall weight of the mat which, for many users, is an important item to be taken during travel, or carried to work.

Typically, yoga mats are about 180 cm long and 60 cm in width, and on average are about 3 mm. in thickness. Nevertheless, yoga mats may range in thickness between lightweight versions which might be 2 mm thick and more robust mats having a thickness of 6 mm, which is strong enough for more vigorous physical activity, and soft and cushiony enough for yoga therapy.

As can be seen from the above discussion, yoga mats carry numerous advantages for those who seek physical and spiritual well-being. More particularly, because they are portable, they may be taken on trips whereby physical training regimens may be performed regardless of location. Yoga mats work well on wood floors, as well as on carpeted areas, tiles, and in public spaces where the floor may be concrete, grass, clay or even gravel. Thus, a disciplined individual may reap the benefits of exercise and meditation in any location.

SUMMARY OF THE INVENTION

In accordance with the invention, it has been recognized that one or more of the performance of yoga, Pilates, calisthenics, in place exercising and diet constitute, for many individuals, the core of their fitness regimen. Those of the above activities that require physical performance are advantageously performed on a mat.

In accordance with the invention, it is also been recognized that even for a well disciplined individual, keeping track of one's physical activity may not be accurately performed. Likewise, even if an individual is so disciplined and so self-regulated as to keep such information on a calendar, one would be tempted to not follow the plan, delay or otherwise not follow a regimen. In addition, other factors, such as exercise, food and the like introduce additional frailties into fitness practices.

In accordance with the invention, these frailties are addressed by a personal trainer device incorporating artificial intelligence features specifically aimed at maximum compliance with a fitness regimen. The inventive device includes multiple direct transducers for monitoring a plurality of body related parameters and activities, thus ensuring the recording of numerous vital statistics and regimen practices, including weight, physical activity such as running in place, performing yoga or calisthenics or Pilates exercises, and body mass index.

At the same time the system provides a number of alphanumeric inputs, such as exercise or other activities not directly detected by the inventive apparatus, dietary intake, liquid intake, swimming, and so forth. In this manner, in accordance with the invention, the totality of a person's physical activity and dietary intake may be collected in one place and used to plan and prompt future action in the dietary and physical activity realm. This information is input into the inventive system using an alphanumeric input device, such as a smart phone, which may be connected to the inventive mat by Bluetooth® technology. In accordance with the invention, functionality of the inventive method may be substantially maintained in the inventive exercise device or within the smart phone, and an app used to implement the same.

A third functionality involves crosschecking information, input into the system by the alphanumeric inputs made into the smart phone by the user, against objective measurements taken by the system. For example, intake of water or other liquids, or food can be cross checked against changes in weight, which may be adjusted, for example, by information respecting physical activity. By way of example, if the user has not input the consumption of food or water, but his or her weight has gone up, the system detects this and sends a message prompting the input of the information, perhaps suggesting the type of information which was not input into the system.

Likewise, the input of performance of certain Pilates or yoga activities may be cross checked against sensor information. For example, if the user reports doing a particular Pilates exercise, the switches used to detect trotting in place will have received a certain pattern of actuation consistent with the particular activity entered into the system. Where such detection is absent or inconsistent, an artificial intelligence algorithm may, optionally in accordance with the invention, sound an alarm and prompt a suggestion to correct an entry by questioning whether the amount of physical activity entered is correct, or prompting the entry of physical activity which was not entered but is indicated as having been performed.

In this manner the integrity, accuracy and completeness of the collected data is maximized.

The inventive capability of the inventive apparatus, for example a mat, stems from the suitability of the inventive apparatus for different activities. However, different activities are most effectively performed with different types of mats. For example, most yoga mats are over 6 mm in thickness. On the other hand Pilates mats, which because of the nature Pilates, are best performed on a mat which cushions the more sensitive body parts during the exercise, are usually thicker, typically between 8 mm and 15 mm. For a universal mat of the type of the present invention, a mat thickness in the range of 4-8 mm is a good compromise. A mat between 5 mm and 7 mm should work very well overall, perhaps roughly being about 6 mm, which is perhaps ideal for diverse purposes. For universal use, a rubbery spongy material is preferred for its cushioning characteristics. Such material provides both grip and cushioning.

In accordance with the invention, it is contemplated that the inventive device will interface with a smart device, such as a smart phone, personal computer, iPod, iPad or other smart device using Wi-Fi or Bluetooth technology.

In accordance with the invention, a method and apparatus are provided for mechanized personal training. More particularly, the inventive apparatus comprises a mat member. The mat includes a scale physically secured to the mat member. The scale has an electrical output strives an electronic circuit. A display displays a weight measured by the scale. A switch is distributed over an area roughly commensurate with the area needed to trot in place. The switch is secured to the mat and underlies a top surface of the mat. The switch is coupled to the electronic circuit. The electronic circuit is programmed to count the number of times that the switch is closed, whereby trotting in place results in closing the switch in response to trotting paces. The above transducers are used to monitor and crosscheck activity and dietary information input into the system by the user and make recommendations. The switch comprises a pair of switches, each of the switches comprising two separate switch members, each of the separate switch members being positioned to respond to one of the feet of a user trotting on the mat. The separate switch members are separated by spacers, and trotting on the mat causes the switch members to come into electrical contact with each other triggering the counting of a step by the electronic circuit. The scale comprises a pair of transducers, one positioned to be stood on by the left foot during a weighing operation and the other positioned to be stood on by the right foot during a weighing operation.

A wireless interface allows control of the electronic circuit by a smart device. The wireless interface may be Bluetooth® and/or Wi-Fi.

To avoid damage, the electronic circuit is displaced from the scale greater than 20 cm.

The scale may comprises first and second rigid members, the first and second rigid members being positioned in facing spaced relationship to each other. The sheet member may comprise a bottom sheet member and a top mat member. The mat member may further comprise a cushion member disposed between the bottom sheet member and the top sheet member. The cushion member defines cutouts for the scale.

A switch may be distributed over an area roughly commensurate with the area needed to trot in place. In accordance with the invention, the switch may be secured to the mat and underlie a top surface of the mat. The switch is coupled to the electronic circuit, and the electronic circuit is programmed to count the number of times that the switch is closed, whereby trotting in place results in closing the switch in response to trotting paces. The switch may be positioned within a second cut out within the cushion member.

The electronic circuit includes non-volatile memory programmed to execute an artificial intelligence algorithm to the weight and trotting information from the scale and the switch, and in response thereto generate, at intervals in time, activity and dietary suggestions.

In accordance with the invention, user preferences selected from the group consisting of favorite foods, favorite exercises, favorite activities, and best times for conducting various activities may be stored in non-volatile memory for access by the electronic circuit and used to generate suggest activity and/or dietary actions.

The circuit is programmed with instructions in the non-volatile memory to correlate information collected by the scale and the switch to judge the completeness of information input into the system, prompt the entry for correction of information in the system, and on the basis of corrected information move to generate activity and/or dietary suggestions.

The electronic circuit is programmed to receive weight information from the scalet. The circuit includes non-volatile memory programmed to apply an artificial intelligence algorithm to the weight information from the scale, and in response thereto generate, at intervals and time, activity and dietary suggestions.

BRIEF DESCRIPTION OF THE DRAWINGS

The structure and use of the inventive mat will become apparent from the following description taken in conjunction with the drawings, in which.

DETAILED DESCRIPTION OF THE PREFERRED EMBODIMENTS

Referring first to FIGS. 1 to 4, the inventive personal trainer device takes the form of a mat 10. Mat 10 comprises a bottom mat member 12 and a top mat member 14.

Figure 1:
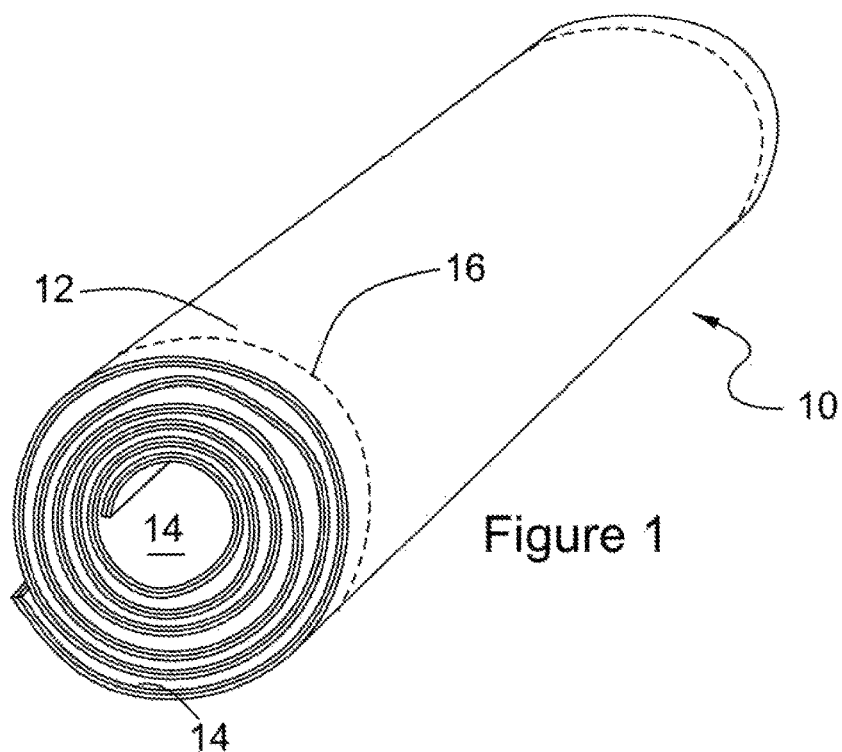
FIG. 1 is a perspective view of a personal trainer device taking the form of a yoga mat in a rolled up configuration for easy portability and representing a general implementation of the present invention.
Figure 2:
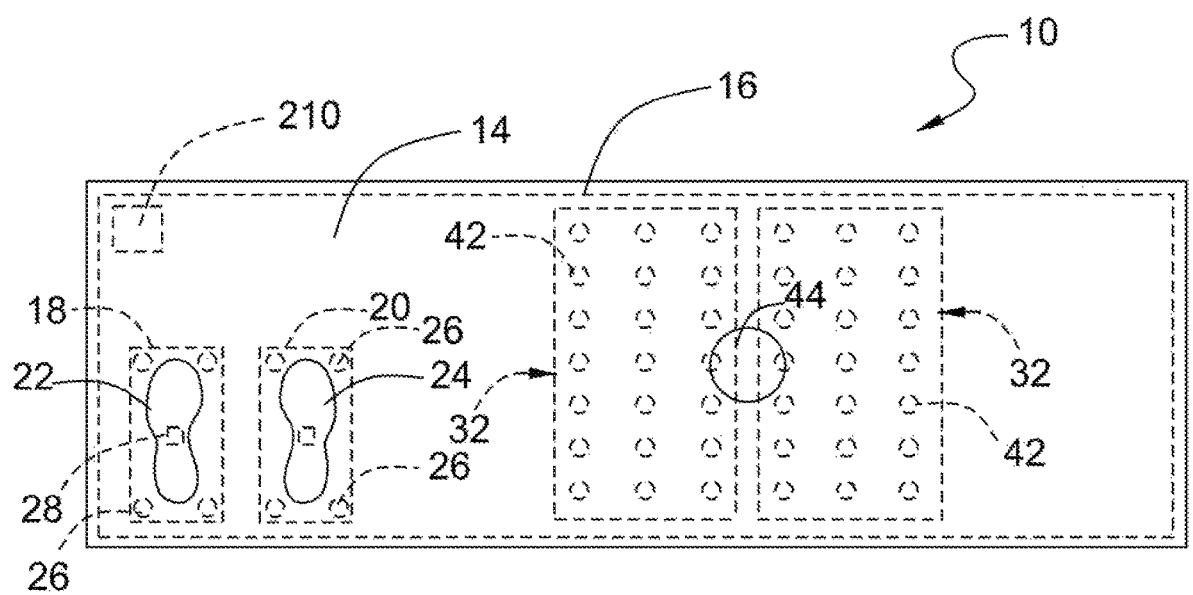
FIG. 2 is a top plan view of the inventive personal trainer device.
Figure 3:
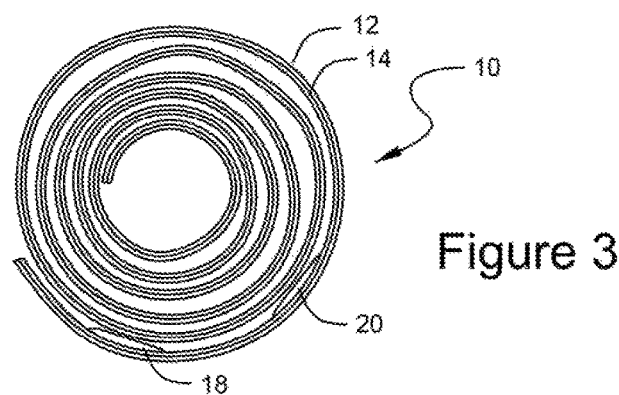
FIG. 3 is a side view of the rolled up inventive personal trainer mat.

As shown in FIG. 2, bottom mat member 12 is sewn to top mat member 14 by stitching 16. The left foot scale 18 and a right foot scale 20 are positioned between bottom mat member 12 and top mat member 14. Foot position is guided by a printed or screened image of the left foot 22 and a printed or screened image of a right foot 24 which is imprinted on top mat member 14. Bottom mat member 12 and top mat member 14 may be made of any suitable material, such as vinyl, a polymeric film, a rubber film and so forth. In addition, other materials such as hessian, textile or the like maybe use. In accordance with a preferred embodiment of the invention, a substantially nonporous material, such as vinyl or another polymeric film, has the advantage of being easy to clean and disinfect. Heat sealing of the periphery of bottom mat member 12 to the periphery of top mat member 14 provides an added degree of safety in terms of locking out potential pathogens and allowing an alcohol wipe down of the top mat member 14 and bottom of mat member 12, together with a wipe down of the peripheral edge, to effectively remove pathogens from mat 10.

Left foot scale 18 and a right foot scale 20 both each include four balance pads 26. Left foot scale 18 and a right foot scale 20 each both include a single weight transducer 28, for example a conventional piezoelectric transducer. Alternatively, a variable resistance strain gauge, an electro-capacitive gauge or other transducer may be used.

In accordance with the preferred embodiment of the invention means are also provided for measuring body mass index. This can be done, for example, by having the individual input his or her height into the inventive system, and then the system doing the customary calculation based on the input height and the detected weight. In accordance with the invention, individual left foot and right foot scales 18 and 20 are provided so that there is sufficient area for the support two individual human feet, while, at the same time, allowing the region of the mat between the left and right foot scales to flex or bend providing for easy rollability of the finished inventive mat 10 for storage, travel, portability and other purposes requiring a compact configuration.

Figure 4:
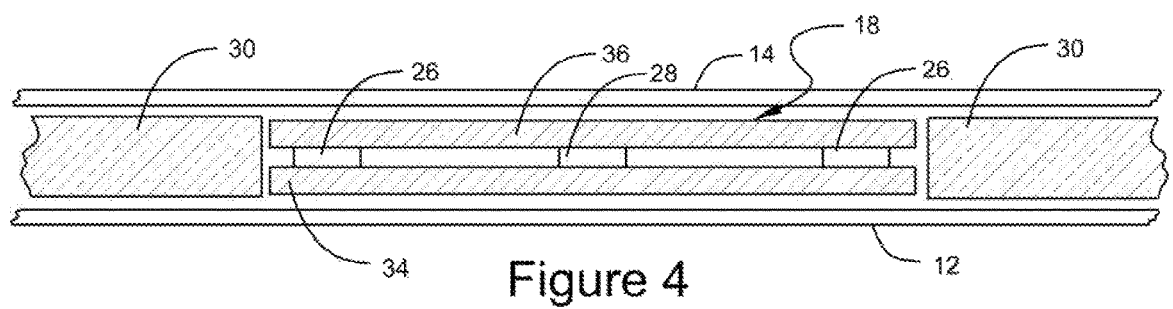
FIG. 4 is a cross-sectional view illustrating the structure of a scale in a personal trainer mat implemented according to the present invention.

As illustrated in FIG. 4, bottom mat member 12 and top mat 14 may be made of any suitable material, such as woven straw, hessian, textile, vinyl or other suitable material. A compressible rubbery dense phone cushion 30 is disposed between bottom mat member 12 and top mat 14. Cushion 30 underlies the entire top mat member 14 except for cutout areas which accommodate individual left foot and right foot scales 18 and 20, and a third cutout area for a footsteps detector switch 32, as appears more fully below. In accordance with the invention, cushion 30 has a thickness of about 5 mm. Bottom mat member 12 has a thickness of about 0.5 mm. Likewise top mat member 14 also has a thickness of about 0.5 mm.

Each of the individual left foot and right foot scales 18 and 20 comprise a lower plate member 34 and an upper plate member 36. Lower plate member 34 and upper plate member 36 are sheet members, for example substantially rigid steel plates having a thickness of 2.5 mm.

During use of the scale, the user puts his left foot on scale 18 and his right foot on scale 20. The weight detected by both scales is added to determine the actual weight of the individual. Thus, the right and left foot scales effectively act together as a single scale. In addition, as is set forth in greater detail below, a smart phone used with the inventive mat 10 may receive an input indicating the height of the user, whereby body mass index may be calculated.

Figure 5:
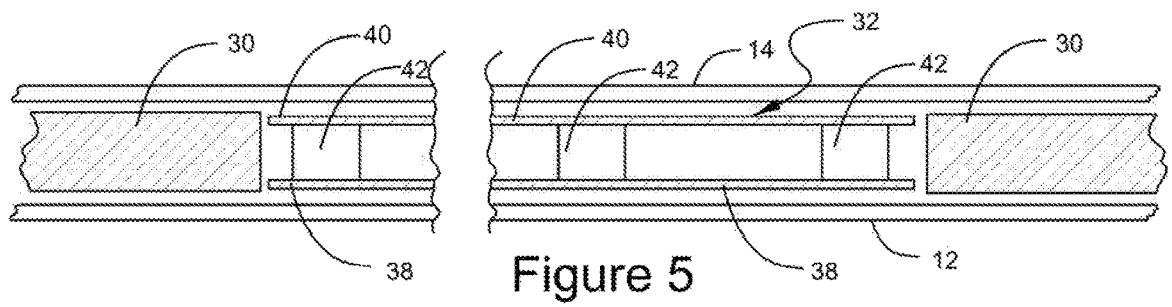
FIG. 5 is a cross-sectional view illustrating the structure of a footstep detector for counting paces when trotting in place in a personal trainer mat implemented according to the present invention.

As illustrated in FIG. 5, the mat of the present invention includes a pair of footstep detector switches 32. One of the switches 32 functions as a detector of steps made by the left foot, while the other of the switches 32 functions as a detector of steps made by the right foot. Each of the switches 32 comprises a pair of thin flexible copper beryllium sheets, namely, a bottom copper-beryllium sheet 38 and a top copper-beryllium sheet 40. Bottom copper-beryllium sheet 38 is positioned in facing spaced relationship to top copper-beryllium sheet 40. Spacing between bottom copper-beryllium sheet 38 and top copper-beryllium sheet 40 is maintained by a plurality of foam plastic spacers 42, made, for example, of open cell polyurethane foam. The general indication of where the individual is to stand is printed on top mat 14, for example as a silkscreened circle 44. When the user is trotting in place, the bottom and top copper beryllium sheets 38 and 44 point of contact with each other thus resulting in the recording of a debt by the user while he or she is trotting in place.

In accordance with the invention, functioning of the mechanized trainer mat 10 is controlled by a smart device 210 comprising a central processing unit, programming capability and appropriate interfaces as are described below.

Smart computing circuit 210 is placed in an out-of-the-way position where it is unlikely to be stepped on during the time that the individual is weighing himself or herself. Nevertheless, circuit 210 is, advantageously, housed in a rigid, for example steel, case to protect it against physical impact. Likewise, it is sealed to protect against water and other hazards. Nevertheless, during the most heavy exercise using the inventive mechanized trainer mat 10, trotting in place, it is even further removed from the activity. More particularly, it is displaced further from the area of activity when the individual is trotting in place, than it is from the area where the individual stands while using the scales to measure the user's bodyweight. Given the rigidity of the steel case, while it is unlikely to be subjected to impacts or even significant pressure during yoga, calisthenics, or Pilates exercise, should such incidental impacts occur it is well protected. This is of particular value, insofar as the inventive mechanized trainer mat 10 is often on the floor.

Figure 6:
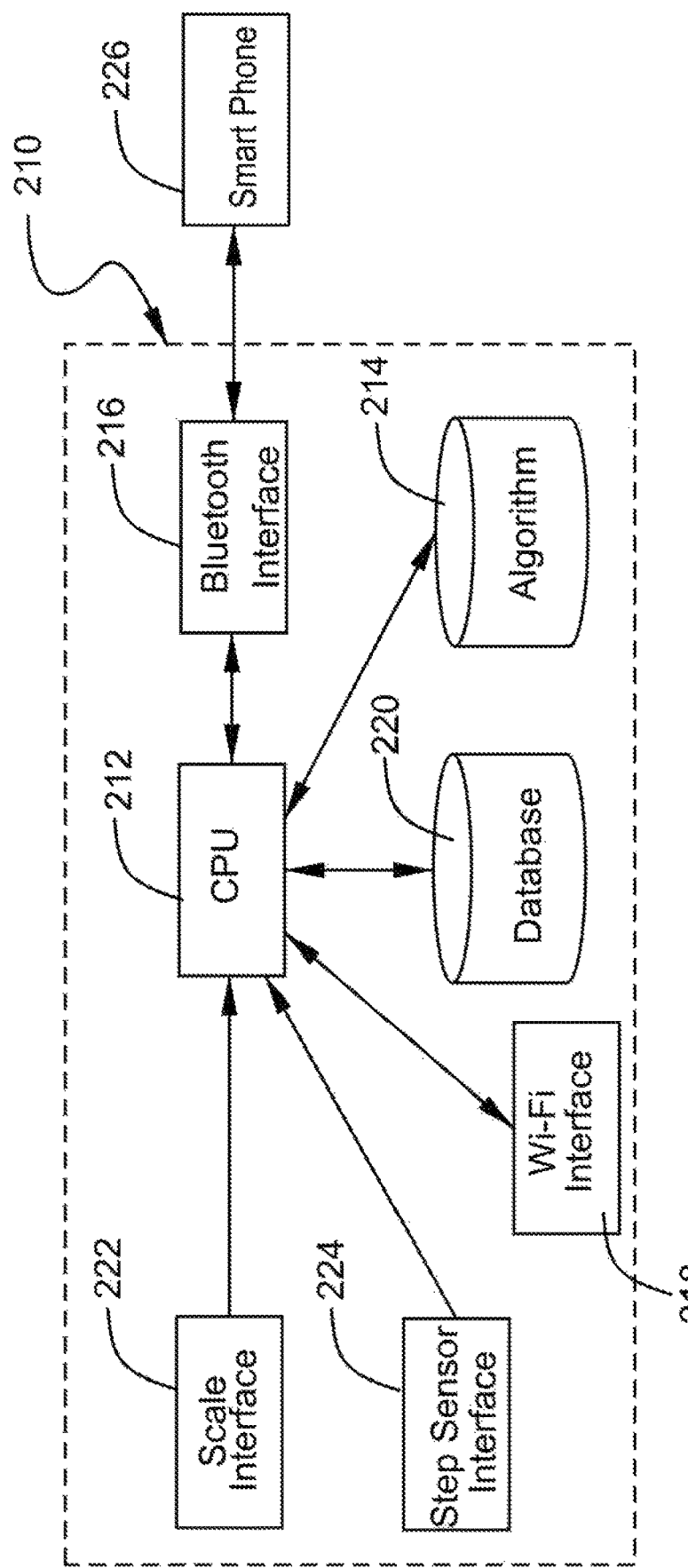
FIG. 6 is a block diagram of the inventive electronic hardware associated with the personal trainer mat illustrated in FIGS. 1-5.

Turning to FIG. 6, the structure of the circuitry of the computing circuit 210 for mechanized trainer mat 10 may be understood. More particularly, computing circuit 210 comprises a central processing unit 212, which may be of any of the various types used in various smart devices. The operation of computing circuit 210 is controlled by a software program which is stored on non-volatile memory device 214.

Central processing unit 212 communicates with a smart phone 216, or an other smart device such as an iPad, iPod, Android pad or personal computer by, for example, Bluetooth interface 216.

Likewise, central processing unit 212 communicates with the Internet via a Wi-Fi interface 218. In accordance with the invention, it is contemplated that remote access to functionality, whether it is stored on the cloud or other device may be accessed remotely via the Internet. More particularly, during operation of the inventive device, information detected and input into the system is periodically uploaded to the cloud, where the user may access the same via the Internet using his smart phone or other paired device, regardless of location and regardless of the location of the inventive mat 10.

While inventive mat 10 may be programmed via the Internet, in accordance with the preferred embodiment, programming of mat 10 is done using Bluetooth interface 216, whereby the functionalities of the inventive trainer mat 10 may be accessed whether or not there is access to Wi-Fi or the Internet.

Functionality of the inventive mechanized trainer mat 210 is enabled by access to a plurality of databases 220, which enable various functionalities as covered in greater detail below. Access to scales 18 and 20, and step sensor 32 is provided by scale interface 222 and step sensor interface 224, respectively.

As mentioned above, the inventive mechanized trainer mat 10 is controlled by, for example, a smart phone 226 over a Bluetooth connection provided by smart phone 226 and/or Bluetooth interface 216. In accordance with the invention, it is contemplated that smart phone 226 will have an application, which was downloaded over the Internet, installed on it. Smart phone 226 provides control functions and information access in a manner typical of smart devices which are controlled by smart phones.

Figure 7:
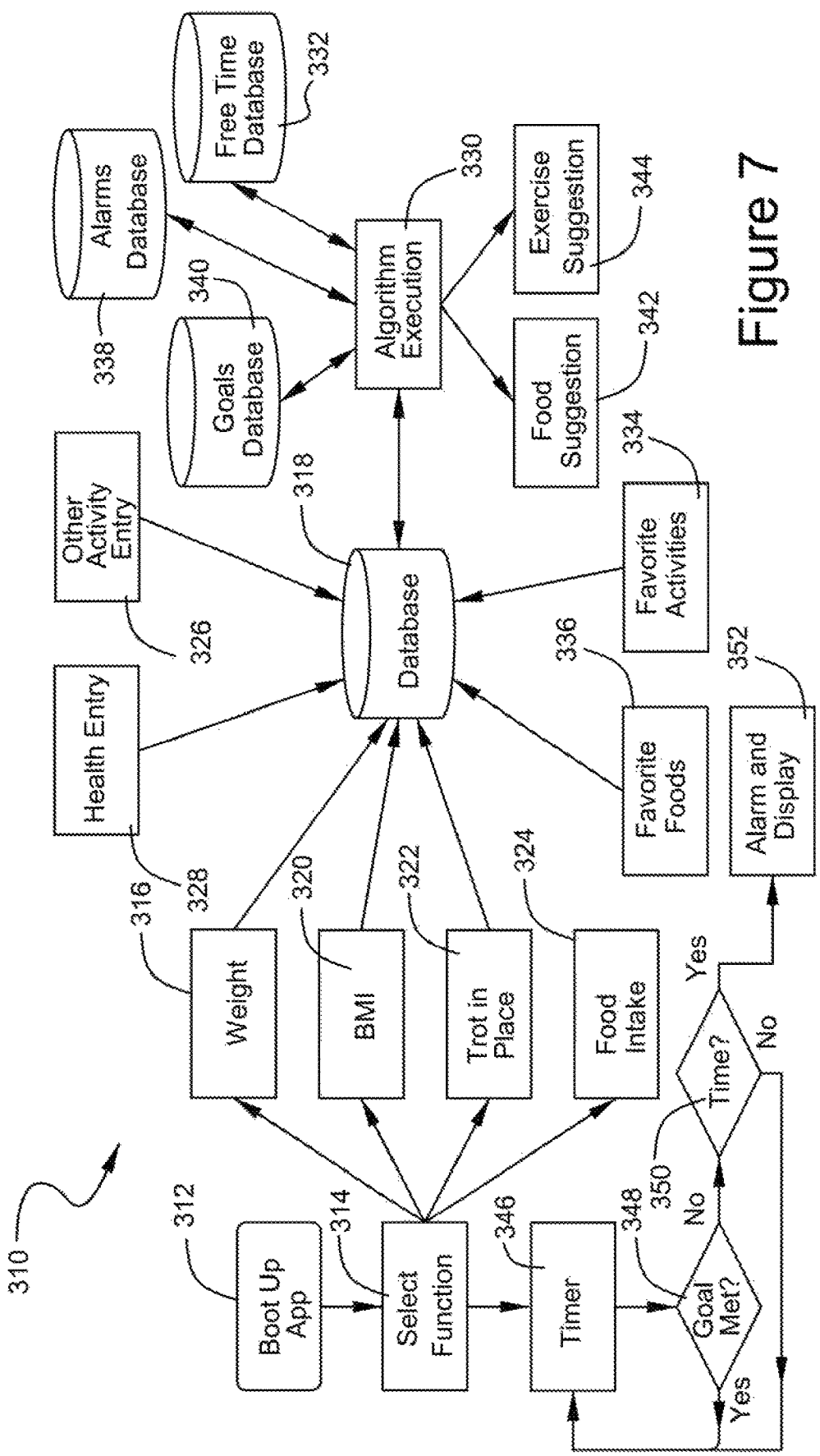
FIG. 7 is a flow chart illustrating the method of the present invention in the form of software stored on a non-volatile memory component in the inventive system.

The method 310 of the operation of the inventive system may be understood with reference to FIG. 7. More particularly, method 310 initiates with boot up of the application on the smart phone at step 312. After boot up, the application presents a select screen to the user at step 314 inviting a selection of various options by presenting a plurality of virtual touch sensitive buttons on the screen of the smart phone, each button being associated with a particular option. The operation of method 310 is controlled by communicating with a non-volatile programming memory at step 330, as is more fully detail below.

In the event that the user wants to know his or her weight or to have that weight recorded in the system, at step 316, actuation of the appropriate button displayed on the screen of the smart phone causes the system to display the weight and input it into a database at step 318. Alternatively, the weighing function and storage of the weight may be done simply in response to use of scales 16 and 18 and the detection of a weight which is within a range expected to be the weight of the individual based on historical data stored at step 318.

Another option presented to the user at step 314 may be checking of the body mass index. Upon selection by the user at step 320, the system calculates the body mass index and displays the same on the user's smart phone.

Another option presented to the user is to specify at step 322 a particular activity associated with the inventive trainer mat 10, that is an activity whose performance can be monitored by mat 10, for example trotting in place, doing a particular yoga position, performing a Pilates exercise or doing another activity which can be sensed by mat 10. If desired additional transducers for detecting action may be provided. Similarly, the user may choose to input an eating decision at step 324. In all cases, the activity, weight, body mass index, food consumed, or other data input in the system is stored at step 318.

The user is also given the opportunity to input at step 326 an activity which cannot be monitored by the various sensors on mat. Such an activity might be swimming, playing golf, dancing, and so forth.

In accordance with the invention, it is also contemplated that the user will input health information at step 328. More particularly, such information may be HDL and LDL cholesterol levels, triglyceride levels, or other health data. Such information is input into the system in order to allow the artificial intelligence algorithm to control the method at step 330.

In accordance with the invention, mechanized trainer mat 10 uses user input and collected data, including weight, body mass index, exercises performed, health information input by the user, meal information and copies, and so forth to construct a diet and exercise regimen which is periodically prompted to the user.

To enable this with a degree of rigor, the user inputs, in addition to the inputs described above, such things as the user's available free time at step 332. Likewise, favorite activities, such as swimming, golf, yoga boating or the like, are input at step 334. At step 336 the user can input his or her favorite foods to enable the artificial intelligence algorithm to design meal suggestions which are more likely to be followed.

In addition, at step 338 the user can select those times when he or she wishes to be reminded respecting exercise, meals, or the like. The object of such user input is to ensure that any notifications and alarms occur at a point in time where they can be acted upon. For example, if the user is a student, alarms would be scheduled for times outside the time typically used for classwork.

U the user ser is also given the opportunity to inform the artificial intelligence algorithm respecting goals at step 340. Such goals may be lower cholesterol, lower triglycerides, a particular body weight, a particular body mass index, user specific nutrition objectives, the taking of certain medications, etc. Using such information, the artificial intelligence algorithm determines recommended actions.

Using such information, the system may prompt the individual when required, for example when receiving a query with respect to a food suggestion at step 342 suggesting an appropriate food, based on a database of, for example, preferred foods, and their caloric and nutritive values. Likewise, the system may provide a physical activity suggestion when queried by the user at step 344.

In the event that the system is not receiving information with respect to physical activity, at certain times the system at step 346 gathers available data to proceed at step 348 to determine if goals have been met. It goals have been met, the system returns to its timing operation at step 346. On the other hand, if exercise or other appropriate action is required the system proceeds to step 350 where the system determines whether the present time is an appropriate one for sounding an alarm and prodding achievement of a goal. If it is not, at an appropriate time the system proceeds back to monitoring the system through the use of sequential timing checks at step 346.

On the other hand, if the time is appropriate, the system proceeds to step 352 where, for example, an audible alarm, alphanumeric display, email message, etc. is created for the user and contains a prompt to do, for example, the desirable activity, such as trotting in place, checking weight, performing exercises, and so forth.

In accordance with the invention, it is contemplated that the inventive mat will be powered by a replaceable rechargeable battery which may be charged using a conventional USB power supply. Alternatively, wireless recharging may be implemented in a manner well known in the battery power supply art. It is also contemplated that the electronics in inventive mat 10 may also be connected with, for example, a personal computer by a cable, for example a USB A, B or C cable.

While illustrative embodiments of the invention have been described, it is noted that various modifications will be apparent to those of ordinary skill in the art in view of the above description and drawings. Such modifications are within the scope of the invention which is limited and defined only by the following claims.

What is claimed:

1. Apparatus, comprising:
   (a) a mat member;
   (b) a scale physically secured to said mat member and having an electrical output;
   (c) an electronic circuit receiving the output of said scale;
   (d) a display for displaying a weight measured by said scale; and
   (e) a switch distributed over an area roughly commensurate with the area needed to trot in place, said switch being secured to said mat and underlie a top surface of said mat, said switch being coupled to said electronic circuit, and said electronic circuit being programmed to count the number of times that the switch is closed, whereby trotting in place results in closing said switch in response to trotting paces.

2. Apparatus as in claim 1, wherein said switch comprises a pair of switches, each of said switches comprising two separate switch members, each of said separate switch members being positioned to respond to one of the feet of a user trotting on said mat, said separate switch members being separated by spacers, and trotting on said mat causes said switch members to come into electrical contact with each other triggering the counting of a step by said electronic circuit.

3. Apparatus, comprising:
   (a) a mat member;
   (b) a scale physically secured to said mat member and having an electrical output;
   (c) an electronic circuit receiving the output of said scale;
   (d) a display for displaying a weight measured by said scale; and
   (e) a switch distributed over an area roughly commensurate with the area needed to trot in place, said switch being secured to said mat and underlie a top surface of said mat, said switch being coupled to said electronic circuit, and said electronic circuit being programmed to count the number of times that the switch is closed, whereby trotting in place results in closing said switch in response to trotting paces to generate trotting information, and said electronic circuit is programmed to receive weight information from said scale, and wherein said electronic circuit includes non-volatile memory programmed to execute an artificial intelligence algorithm to said weight and trotting information from said scale and said switch, and in response thereto generate, at intervals in time, activity and dietary suggestions.

4. Apparatus as in claim 3, wherein user preferences selected from the group consisting of favorite foods, favorite exercises, favorite activities, and best times for conducting various activities are stored in non-volatile memory for access by said electronic circuit and used to generate suggest activity and/or dietary actions.

5. Apparatus as in claim 4, wherein said circuit is programmed with instructions in said non-volatile memory to correlate information collected by said scale and said switch to judge the completeness of information input into the system, prompt the entry for correction of information in the system, and on the basis of corrected information move to generate activity and/or dietary suggestions.

6. Apparatus as in claim 5, wherein if the user has not input the consumption of food or water, but the scale shows that weight the user's weight has gone up, the artificial intelligence algorithm causes the sending of a message prompting the input of the information and suggesting the type of information which was not input the system.

7. Apparatus, comprising:
   (a) a mat member;
   (b) a scale physically secured to said mat member and having an electrical output;
   (c) an electronic circuit receiving the output of said scale;
   (d) a display for displaying a weight measured by said scale; and
   (e) a footsteps detector distributed over an area roughly commensurate with the area needed to trot in place, said footsteps detector being secured to said mat and underlying a top surface of said mat, said footsteps detector being coupled to said electronic circuit, and said electronic circuit being programmed to count the number of times that the switch is closed, whereby trotting in place results in closing said footsteps detector in response to trotting paces, wherein said electronic circuit is programmed to receive weight information from said scale, and wherein said electronic circuit includes non-volatile memory programmed to apply an artificial intelligence algorithm to said weight information from said scale, and in response thereto generate, at intervals and time, activity and dietary suggestions.

8. Apparatus, comprising:
   (a) a mat member;
   (b) a scale physically secured to said mat member and having an electrical output;
   (c) an electronic circuit receiving the output of said scale;
   (d) a display for displaying a weight measured by said scale; and
   (e) a footsteps detector distributed over an area roughly commensurate with the area needed to trot in place, said footsteps detector being secured to said mat and underlying a top surface of said mat, said footsteps detector being coupled to said electronic circuit, and said electronic circuit being programmed to count the number of times that the switch is closed, whereby trotting in place results in closing said footsteps detector in response to trotting paces.

9. Apparatus as in claim 8, wherein said scale comprises a pair of transducers, one positioned to be stood on by the left foot during a weighing operation and the other being positioned to be stood on by the right foot during a weighing operation.

10. Apparatus as in claim 8, further comprising:
    (f) a wireless interface for allowing control of said electronic circuit by a smart device.

11. Apparatus as in claim 10, wherein said wireless interface is Bluetooth®.

12. Apparatus as in claim 10, wherein said wireless interface is a Wi-Fi interface.

13. Apparatus as in claim 8, wherein said electronic circuit is displaced from said scale greater than 20 cm.

14. Apparatus as in claim 8, wherein said scale comprises first and second rigid members, said first and second rigid members being positioned in facing spaced relationship to each other, and wherein said sheet member comprises a bottom sheet member and a top mat member.

15. Apparatus as in claim 14, wherein said mat member further comprises a cushion member disposed between said bottom sheet member and said top sheet member, said cushion member defining cutouts for said scale.

\* \* \* \* \*